(12) United States Patent
Ikeuchi et al.

(10) Patent No.: US 10,431,417 B2
(45) Date of Patent: Oct. 1, 2019

(54) CHARGED PARTICLE BEAM DEVICE AND SAMPLE HOLDER

(71) Applicant: Hitachi High-Technologies Corporation, Minato-ku, Tokyo (JP)

(72) Inventors: Akira Ikeuchi, Tokyo (JP); Shigeru Haneda, Tokyo (JP); Yoshinobu Hoshino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/090,452

(22) PCT Filed: Apr. 13, 2016

(86) PCT No.: PCT/JP2016/061871
§ 371 (c)(1),
(2) Date: Oct. 1, 2018

(87) PCT Pub. No.: WO2017/179145
PCT Pub. Date: Oct. 19, 2017

(65) Prior Publication Data
US 2019/0122853 A1    Apr. 25, 2019

(51) Int. Cl.
*H01J 37/20* (2006.01)
*G01N 1/28* (2006.01)
(Continued)

(52) U.S. Cl.
CPC ............... *H01J 37/20* (2013.01); *G01N 1/28* (2013.01); *H01J 37/22* (2013.01); *H01J 37/222* (2013.01);
(Continued)

(58) Field of Classification Search
CPC .......... H01J 37/20; H01J 37/22; H01J 37/222; H01J 37/28; H01J 2237/20214; G02B 21/26; G01N 1/28
See application file for complete search history.

(56) References Cited

U.S. PATENT DOCUMENTS

| 6,002,136 A * | 12/1999 | Naeem | B82Y 35/00 |
| | | | 250/442.11 |
| 2005/0092933 A1* | 5/2005 | Moriya | H01J 37/20 |
| | | | 250/440.11 |

(Continued)

FOREIGN PATENT DOCUMENTS

JP   3-2551 U   1/1991
JP   2004-245745 A   9/2004
(Continued)

OTHER PUBLICATIONS

International Search Report (PCT/ISA/210) issued in PCT Application No. PCT/JP2016/061871 dated Jul. 5, 2016 with English translation (four pages).

(Continued)

*Primary Examiner* — David E Smith
(74) *Attorney, Agent, or Firm* — Crowell & Moring LLP

(57) ABSTRACT

In order to provide a sample holder capable of easily searching for an observation field of view, the sample holder includes a sample placement portion including a first top surface on which a counterbore part is formed and a rotational axis for rotating the first top surface horizontally, the counterbore part being aligned by being mounted with a sample supporting member having a pattern for alignment, a sample base portion including an opening through which the sample placement portion is capable of moving vertically and a second top surface around the opening, and a sample cover portion which has conductivity and is pressed down toward a direction of the second top surface of the (Continued)

sample base portion, so that a top surface of the sample supporting member placed on the sample placement portion and the second top surface of the sample base portion are flush with each other.

12 Claims, 8 Drawing Sheets

(51) Int. Cl.
*H01J 37/22* (2006.01)
*H01J 37/28* (2006.01)

(52) U.S. Cl.
CPC ..... *H01J 37/28* (2013.01); *H01J 2237/20214* (2013.01)

(56) References Cited

U.S. PATENT DOCUMENTS

| 2013/0105706 | A1* | 5/2013 | Han | G01N 23/04 |
| | | | | 250/442.11 |
| 2016/0217971 | A1* | 7/2016 | Yaguchi | H01J 37/16 |
| 2017/0097291 | A1* | 4/2017 | Selve | B23Q 5/34 |

FOREIGN PATENT DOCUMENTS

| JP | 2011-43417 A | 3/2011 |
| JP | 2014-44967 A | 3/2014 |

OTHER PUBLICATIONS

German-language Written Opinion (PCT/ISA/237) issued in PCT Application No. PCT/JP2016/061871 dated Jul. 5, 2016 (three pages).

* cited by examiner

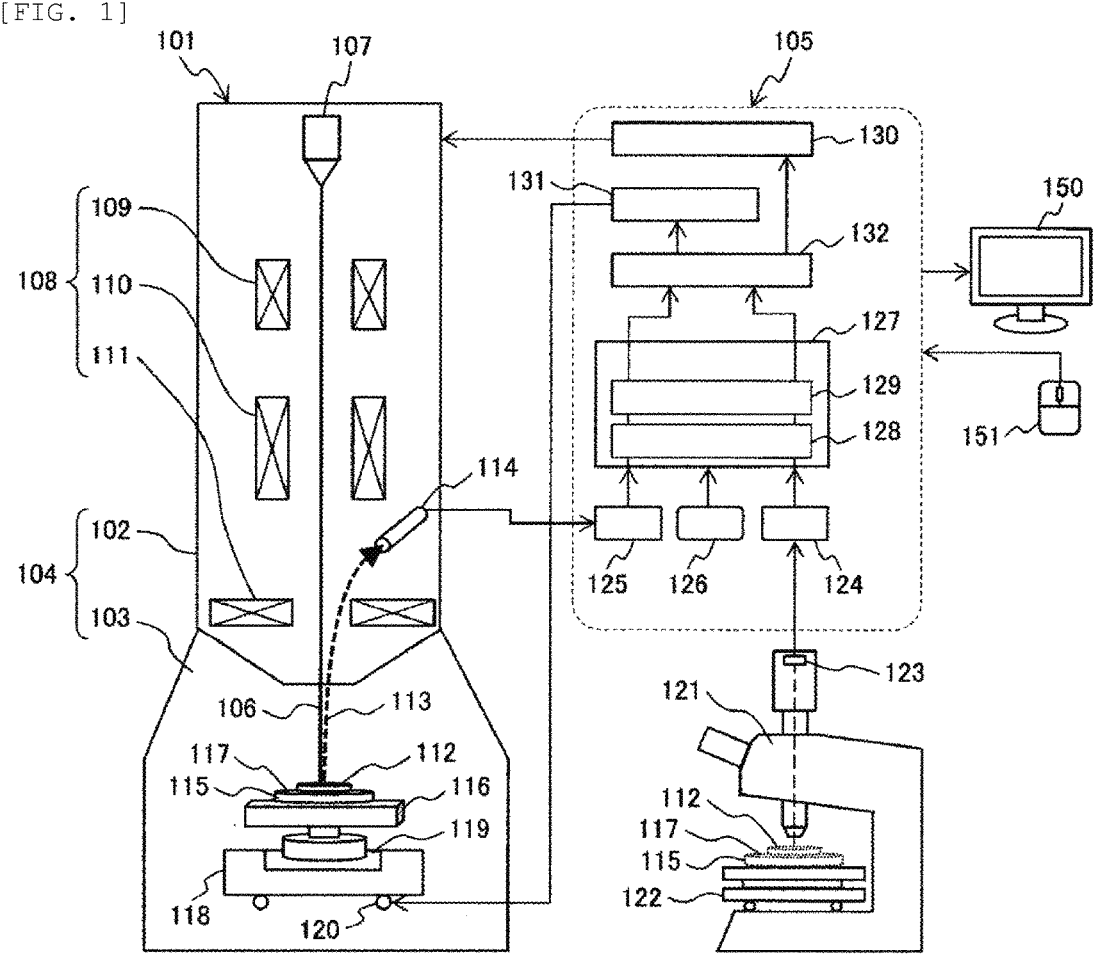
[FIG. 1]

[FIG. 2A]
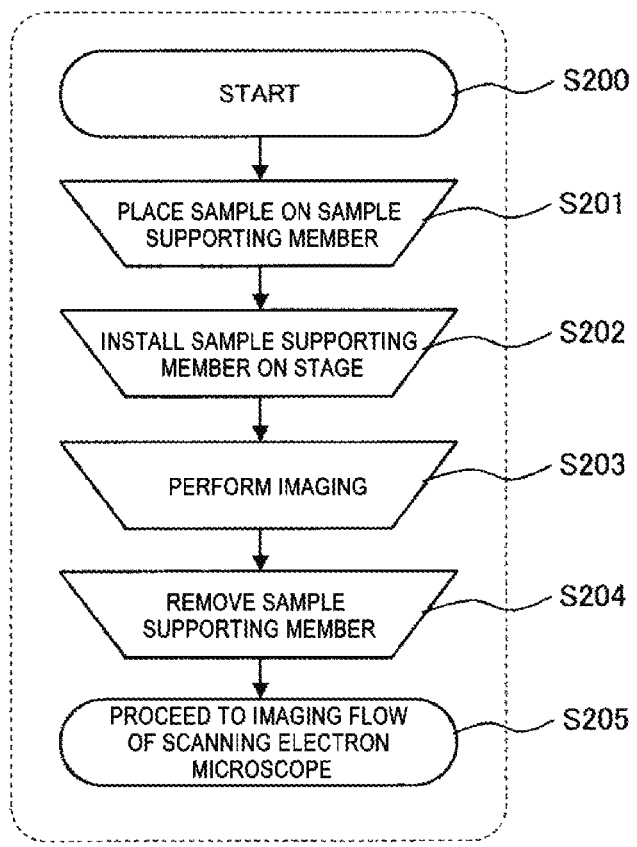

[FIG. 2B]
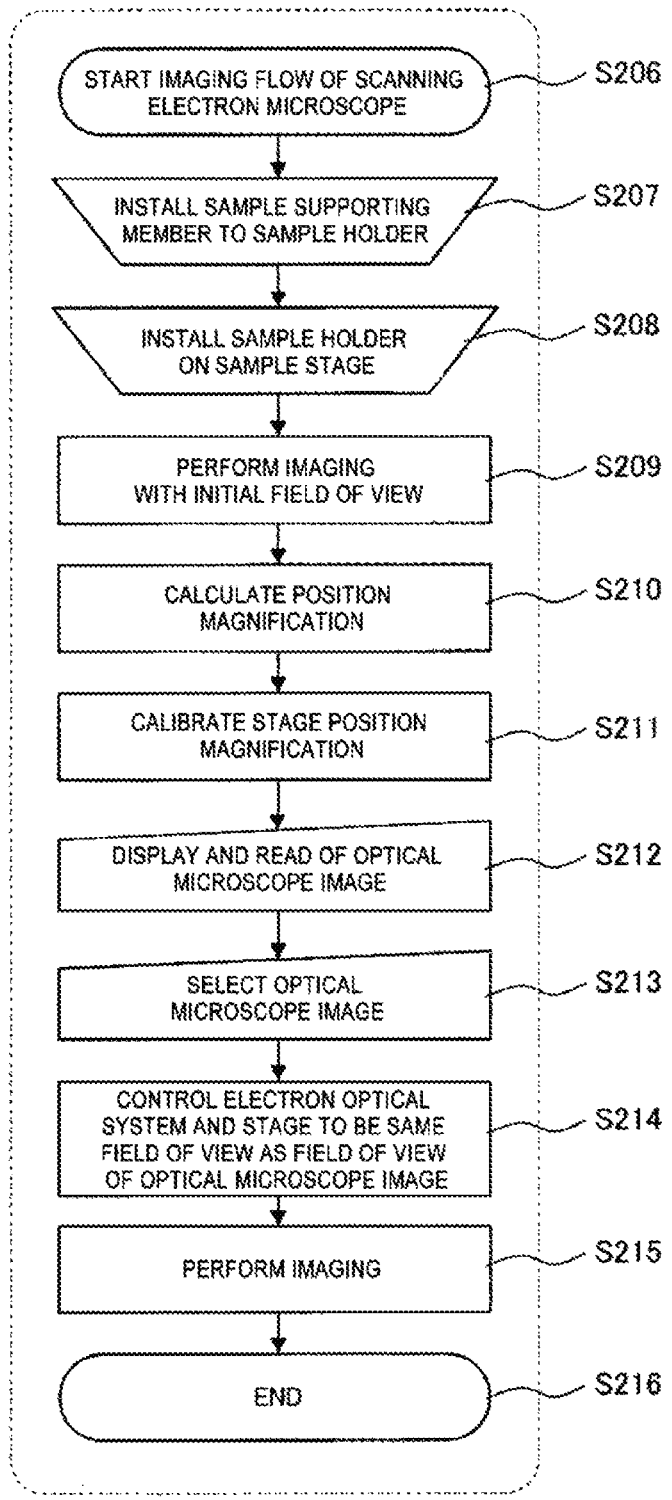

[FIG. 3A]
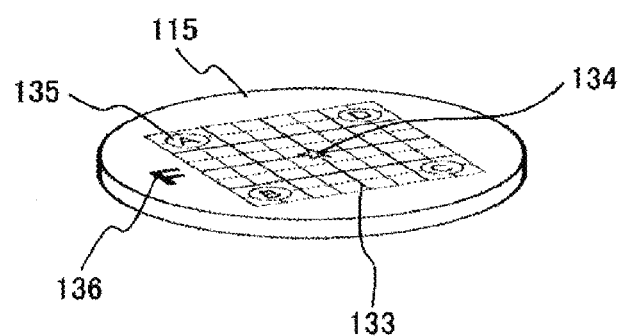
[FIG. 3B]
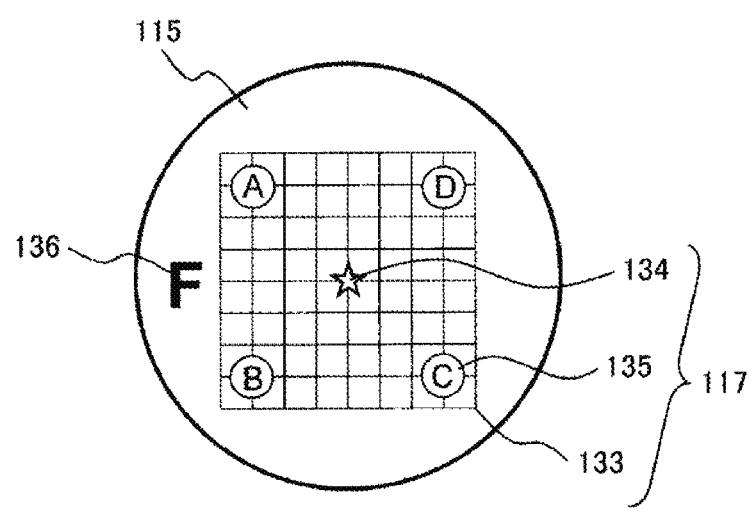

[FIG. 3C]
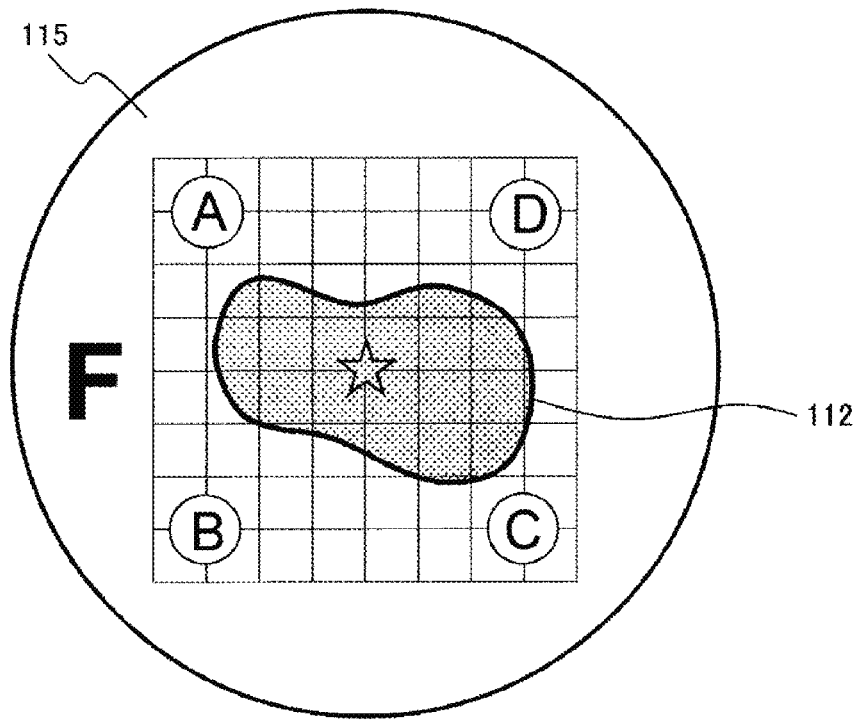
[FIG. 4A]
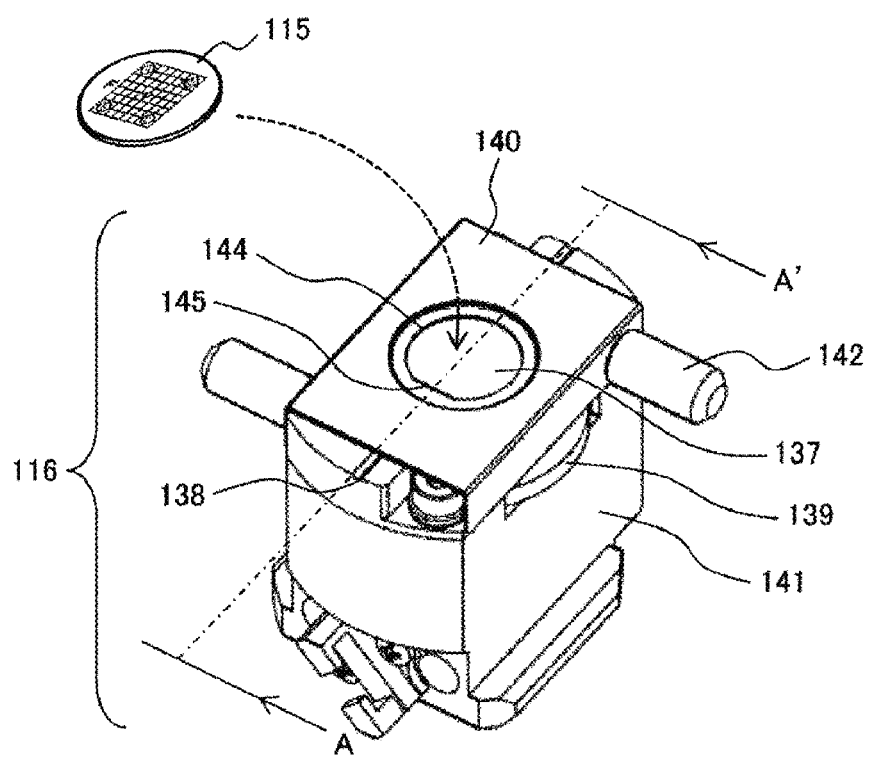

[FIG. 4B]
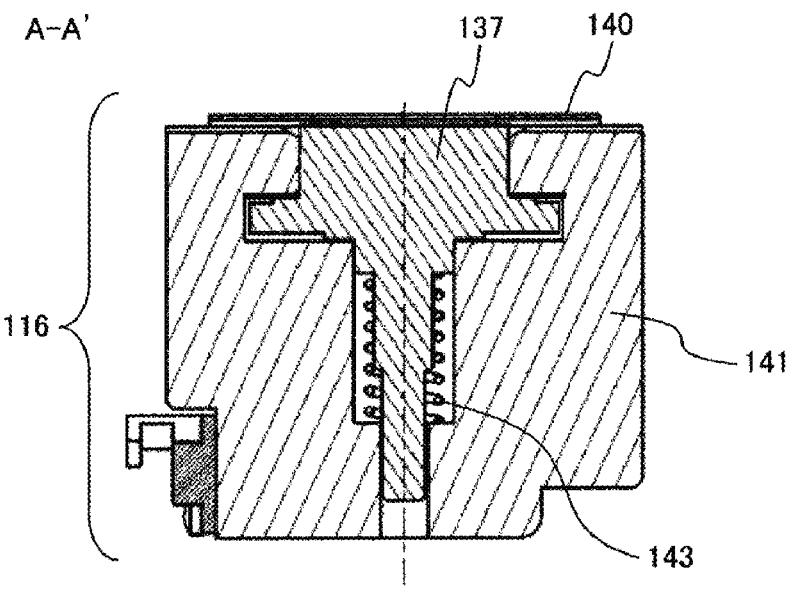
[FIG. 4C]
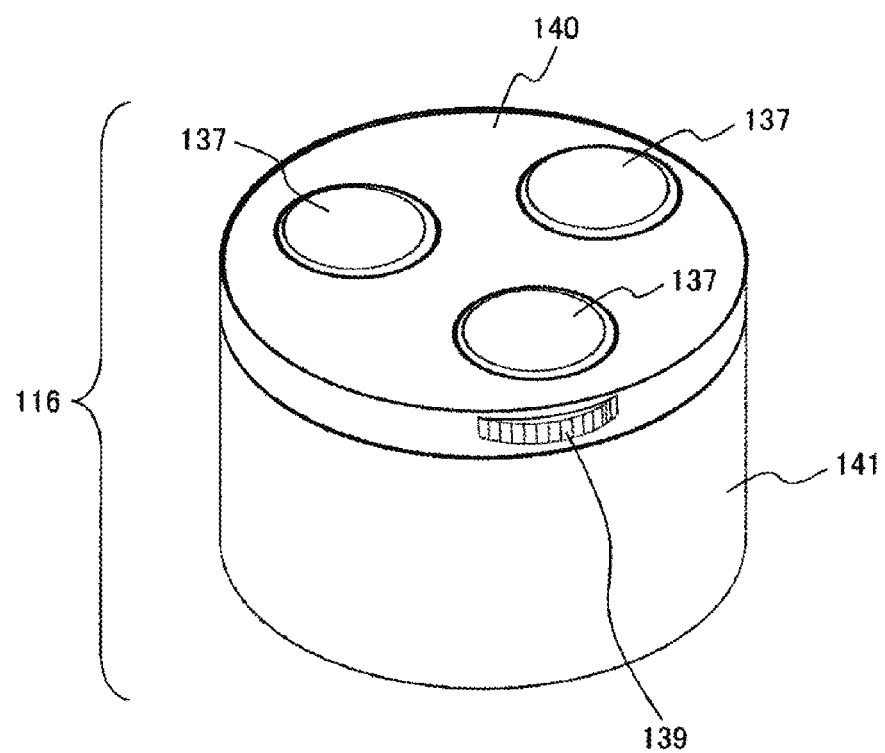

[FIG. 5A]
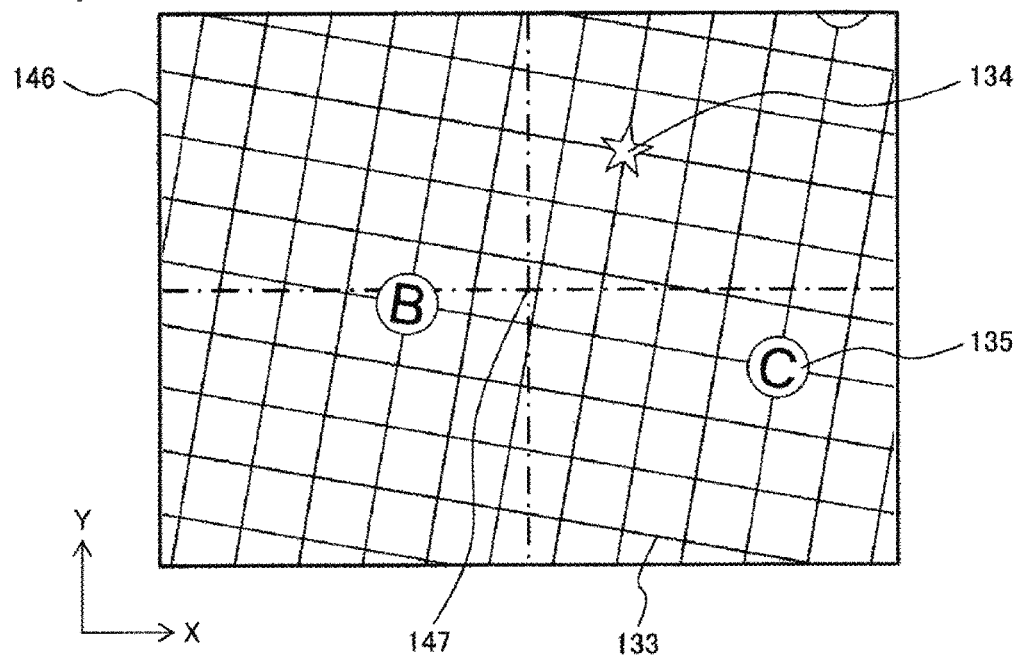
[FIG. 5B]
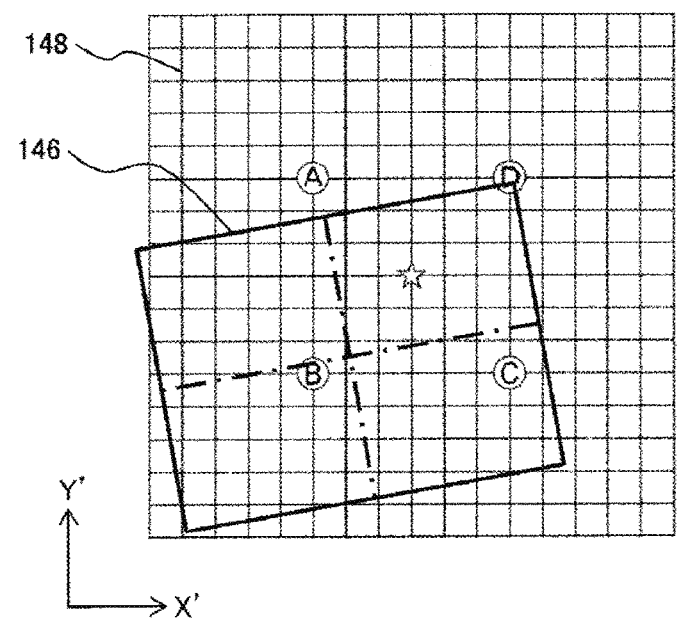

[FIG. 6]
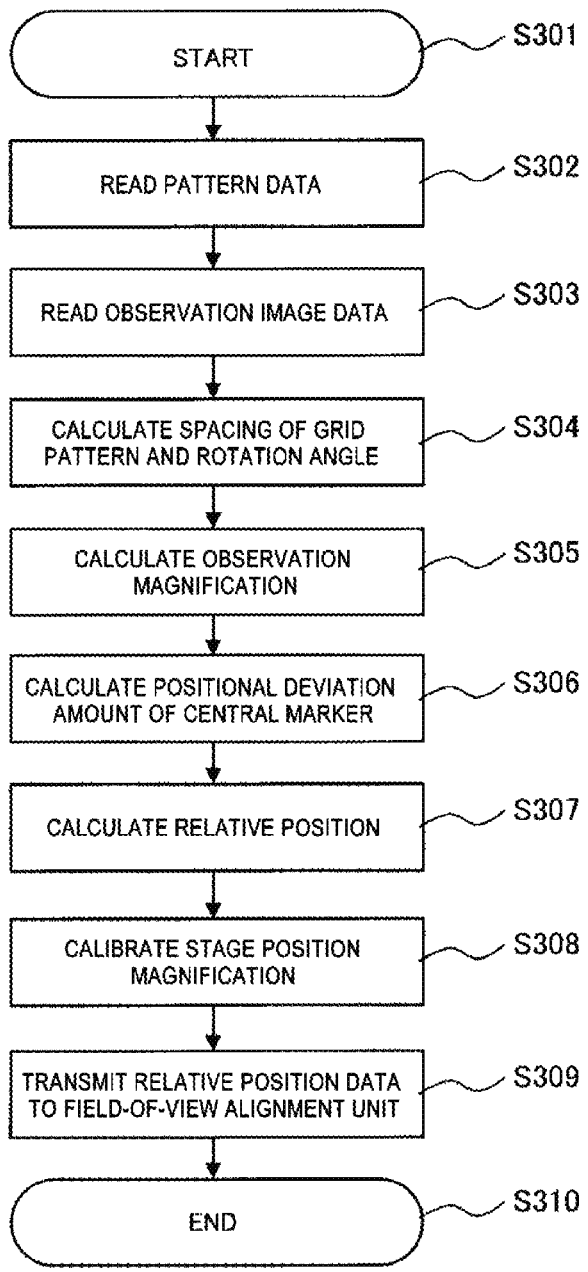

CHARGED PARTICLE BEAM DEVICE AND SAMPLE HOLDER

TECHNICAL FIELD

The present invention relates to a charged particle beam device and a sample holder.

BACKGROUND ART

In a charged particle beam device represented by a scanning electron microscope (hereinafter, referred to as "SEM"), a sample is scanned with a charged particle beam narrowly focused through an electrostatic lens, an electromagnetic lens, or the like to obtain desired information (for example, a sample image) from the sample. When observing a sample with such a device, it is necessary to determine that which position of the sample the current field of view reaches, and move the field of view until a place where the user wants to observe (hereinafter, referred to as "searching for an observation field of view").

In PTL 1, a sample holder for an SEM and an SEM mounted with the sample holder are disclosed which are capable of using a slide glass used for observation with an optical microscope (hereinafter, referred to as "OM") as it is as an observation sample.

CITATION LIST

Patent Literature

PTL 1: JP-A-2014-44967

SUMMARY OF INVENTION

Technical Problem

Since the charged particle beam device uses a charged particle beam having a shorter wavelength than light, it is advantageous in that the charged particle beam device has a higher resolution than OM, so that it is possible to observe a sample (or the structure of a sample) having a size of several nanometers to hundreds of nanometers. On the other hand, depending on the conditions of the electron optical system of the charged particle beam device, it is difficult for the user to search for a field of view. With respect to this problem, PTL 1 discloses a technique to perform observation field-of-view searching by observing the whole view of a sample with the OM prior to observation of the sample with a charged particle beam device, and then observing the sample with a charged particle beam while comparing with the obtained optical image.

However, in PTL 1, when the charged particle beam device performs observation field-of-view searching by using an image captured with the OM (hereinafter, referred to as an "observation position designation image"), a calibration work for making the coordinate system of the observation position designation image on the observation target sample and the coordinate system of the sample stage coincide with each other becomes complicated, which is problematic.

An object of the present invention is to provide a charged particle beam device and a sample holder capable of easily searching for an observation field of view.

Solution to Problem

As an embodiment for achieving the above-described object, there is provided a charged particle beam device including a charged particle source, a sample holder placed with a sample thereon, a charged particle beam optical system in which the sample is irradiated with a charged particle emitted from the charged particle source as a charged particle beam, a detector detecting a signal emitted from the sample, and a controller controlling each constituent element, wherein the sample holder includes a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle, a sample base portion including an opening through which the sample placement portion is capable of moving vertically and a second top surface around the opening, and a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other.

Advantageous Effects of Invention

According to the present invention, it is possible to provide the charged particle beam device and the sample holder capable of searching for the observation field of view.

BRIEF DESCRIPTION OF DRAWINGS

FIG. 1 is a sectional view (partially block diagram) illustrating a configuration example of a system of an SEM.

FIG. 2A is a flow chart illustrating an operation example of OM imaging on an observation target sample.

FIG. 2B is a flow chart illustrating an operation example of SEM imaging on an observation target sample.

FIG. 3A is a bird's eye view illustrating a schematic configuration example of a sample supporting member.

FIG. 3B is a top view illustrating a schematic configuration example of the sample supporting member (without a sample).

FIG. 3C is a top view illustrating a schematic configuration example of the sample supporting member (with a sample).

FIG. 4A is a bird's eye view illustrating a schematic configuration example of a sample holder.

FIG. 4B is a sectional view taken along line A-A' in FIG. 4A.

FIG. 4C is a bird's eye view illustrating another schematic configuration example of a sample holder.

FIG. 5A is a top view illustrating a positional relationship between an initial field of view of an electron microscope image and a pattern for alignment.

FIG. 5B is a top view for describing a positional relationship between pattern data of an electron microscope image and the initial field of view of the electron microscope image.

FIG. 6 is a flow chart illustrating an operation example of a position magnification calculating unit.

DESCRIPTION OF EMBODIMENTS

In examples, an SEM will be exemplified for description as a charged particle beam device, but the charged particle beam device of the invention will not be limited to the SEM. The charged particle beam device according to the invention may set an observation range of a sample from which an observation image is acquired by a charged particle beam device on a captured image of the sample acquired by an imaging device as a field-of-view range, and when an observation range of a sample corresponding to the field-of-view range is irradiated with a charged particle beam by a charged particle beam device to acquire an observation image of the sample, the charged particle beam device may use a shape and dimension information of a pattern which is subjected on a sample supporting member in an observation position designation image used to set the field-of-view range for calibration on irradiation position of the charged particle beam. For example, an example of the charged particle beam device includes a scanning ion microscope, a scanning transmission electron microscope, a transmission electron microscope, a composite apparatus of these with a sample processing device, and an analysis inspection apparatus applied with these devices.

Hereinafter, the charged particle beam device according to examples of the present invention will be described with reference to the drawings. The same symbols indicate the same constituent elements.

Example 1

<System Configuration Example of Charged Particle Beam Device and Imaging Flow>

First, a system configuration example of the charged particle beam device and an imaging flow of an observation target sample will be described with reference to FIG. 1 and FIGS. 2A and 2B.

FIG. 1 is a schematic configuration view illustrating an example of a charged particle beam device (here, a "SEM").

An SEM 101 includes a microscope body 104 configured by integrating a electron beam column 102 and a sample chamber 103 and a control device (controller) 105 controlling each part of the SEM, and the control device 105 is connected with a display unit 150 and an operation unit 151.

The electron beam column 102 is provided with an electron gun 107 for emitting an electron beam 106 and an electron optical system 108 which controls irradiation of the electron beam 106.

The electron optical system 108 includes condenser lenses 109 for focusing the electron beam 106 emitted from the electron gun 107, deflectors 110 for scanning the electron beam 106, and objective lenses 111 for focusing the electron beam 106 so as to be focus on the surface of the surface of a sample 112. In the example of FIG. 1, a detector 114 is also provided which detects a signal 113 (for example, secondary electrons, reflected electrons, and the like) generated when the sample 112 is irradiated with the electron beam 106.

The sample chamber 103 accommodates a sample holder 116 placed with a sample supporting member 115 through an inlet/outlet port capable of opening and closing and not illustrated, and the sample 112 is placed on the sample supporting member 115. The sample supporting member 115 is formed with patterns for alignment 117. The details of the sample supporting member 115 will be described later using the schematic configuration example in a case where the sample supporting member 115 illustrated in FIGS. 3A to 3C has a form of a round cover glass, and the details of the sample holder 116 will be described later with reference to FIGS. 4A to 4C.

The sample holder 116 includes a mechanism capable of easily placing, rotating, and fixing the sample supporting member 115, and includes a mechanism of fixing the sample supporting member 115 such that the patterns for alignment 117 falls within the initial field of view during imaging of the SEM 101. The sample chamber 103 is provided with a sample stage 118 held by the sample holder 116. The sample chamber is evacuated of course.

The sample stage 118 includes an mounted part 119 in which the sample holder 116 is attached detachably and a sample moving mechanism 120 which moves the mounted part 119, for example, in the horizontal plane and in a direction perpendicular to the plane, rotates, or inclines the mounted part inside the sample chamber 103, thereby displacing the position or the orientation of the sample 112 and the sample supporting member 115 inside the sample chamber 103 with the whole sample holder 116. The control device 105 controls the sample moving mechanism 120 and the electron optical system 108, an arbitrary position of the sample 112 is irradiated with the electron beam 106, and the detector 114 detects the generated signal 113, whereby it enables observation with the electron microscope in any position and magnification of the sample.

Here, the magnification described above may be a width of field of view (FOV), a length (pixel size) which one pixel indicates in the case of a digital image, or the like.

The OM 121 is exemplified as an upright type OM in this example, but the OM may be an inverted type OM, and the OM is provided with a stage 122 on which the sample supporting member 115 is placed and an imaging element 123 which obtains image data of an object to be observed. It is obvious that the OM is used under atmospheric pressure.

The stage 122 includes a mechanism which fixes the sample supporting member 115 to a sample supporting member holder (not illustrated) placed with the sample 112 thereon and which moves the sample supporting member 119, for example, in the horizontal plane and in a direction perpendicular to the plane, rotates, or inclines the sample supporting member, thereby displacing the position or the orientation of the sample 112 on the stage 122 with the whole sample supporting member 115. A moving mechanism of the stage 122 may be any of an electric type and a manual type.

The imaging element 123 is, for example, a CCD sensor or a CMOS sensor, and has a function of acquiring imaging data of either a still image or a moving image of the observation target. In this example, it is exemplified that the imaging element 123 is connected to the control device 105 to transmit the captured image data to an image processor for OM (first image processor) 124, but it is not necessary that the imaging element 123 has to be connected to the control device 105, and the imaging element may store the captured image data of an observation target based on the format of the digital image data to transmit the stored image data to an image processor for OM 124.

The control device 105 includes an image processor for SEM (a second image processor) 125 for converting a signal obtained by the detector 114 into observation image data (hereinafter, referred to as "SEM image data"), an image processor for OM 124, and a pattern data storage unit 126 in which shape data of a pattern for alignment is stored.

Each data is read to a position magnification calculating unit 127, magnification of each observation field of view is calculated in a magnification calculating unit 128 by using pattern data, and positional information is calculated in a position calculating unit 129, thereby calculating positional information relative to the pattern coordinates (the calculation executed by the position magnification calculating unit 127 will be described later in detail). By performing calibration of a sample stage 118 using the obtained magnification and the positional information at that time, it is possible to move a sample holder 116 based on the pattern coordinates to image the position designated by the pattern coordinates with a SEM 101.

Also, a field of view and magnification of the observation image data (hereinafter, referred to as "OM image data") obtained by the OM 121 are likewise associated with the pattern coordinates. The information on these magnification and pattern coordinates is set to an electron optical system controller 130 and a sample stage controller 131, and thus it is possible to image the same field of view as the OM image with the SEM 101. A field-of-view alignment unit 132 executes the above-described positional information calculation and instructions to the respective controllers for obtaining the same field of view.

The field-of-view alignment unit 132 transmits the stage position with the same field of view as the OM image and a setting parameter of observation magnification to the sample stage controller 131 and the electron optical system controller 130 based on the information on the field-of-view position of the OM image calculated in the position magnification calculating unit 127.

The above is the outline of an example of the SEM system illustrated in FIG. 1.

Here, according to PTL 1, when the charged particle beam device performs observation field-of-view searching using the observation position designation image, for a calibration work to make the coordinate system of the observation position designation image and the coordinate system of the sample stage coincide with each other on the observation target sample, it is necessary to capture the whole view of the slide glass serving as a sample supporting member placed with a sample with an optical imaging device to use as a reference image. In addition, since it is necessary to capture the reference image with a predetermined field of view and magnification, an optical imaging device in which a field of view and magnification are fixed in advance for capturing the reference image is needed. For this reason, the minimum magnification upon observation of the sample is determined, there is a concern that the whole view of the sample cannot be observed, and it becomes difficult to search for the field of view. Further, when performing a calibration work using the observation position designation image, it is necessary to perform a complicated work of searching for feature points of the observation position designation image from the observation image of the charged particle beam device to associate the feature points of each reference with a plurality of places.

In the example, the following imaging operation is performed using the above-described SEM system example.

FIGS. 2A and 2B are respectively a flow chart of an imaging operation with the OM and a flow chart illustrating an imaging operation when executing observation in the same field of view as a field of view of the OM image obtained thereby with the SEM, in the example using the SEM system illustrated in FIG. 1.

When it is started (step S200), first, the sample 112 is placed on the sample supporting member 115 (step S201), and the sample supporting member 115 is installed on a stage 122 of the OM (step S202). By performing imaging in this state, an OM image of a sample 112 and a pattern for alignment 117 can be obtained. At this time, in a case of low magnification imaging, the imaging is performed in a field of view illustrated in FIG. 3B in which a grid pattern 133 and a central marker 134 are included, and in a case of high magnification imaging, the imaging is performed in a field of view in which the grid pattern 133 and the central marker 134 or an address marker 135 are included (step S203). Accordingly, it is possible to calculate the positional relationship between the OM image field of view and the pattern for alignment 117 in the position magnification calculating unit 127 with respect to the OM image obtained with low magnification or high magnification. The grid spacing in the grid pattern is set to a value in which two straight lines or more are included in the initial field of view. In this example, it is not necessary to capture the whole view of the sample. After imaging is ended, the sample supporting member 115 is removed from the stage 122 (step S204), to proceed to a SEM imaging flow (step S205).

The imaging flow with the SEM is started (step S206), the sample supporting member 115 which has removed from the stage 122 of the OM 121 is installed on a sample holder 116 for SEM (step S207). In this state, first, front and back sides of the sample supporting member 115 is checked with a front and back direction recognition marker 136 as illustrated in FIG. 3B, and the sample supporting member 115 is placed on a sample placement portion 137 as illustrated in FIG. 4. In order to align the horizontal direction of the sample supporting member 115 with the horizontal direction of the sample holder 116, groove processing 138 indicating the horizontal direction of the sample holder 116 is guided to adjust the horizontal direction of the sample supporting member 115 using a rotary knob 139, and finally the sample supporting member 115 is fixed to the sample holder 116 using a sample cover portion 140. Through this step, alignment of the sample supporting member with the sample holder, that is, alignment of the central marker with a rotational axis of the sample placement portion is performed.

Subsequently, the sample holder 116 is mounted on the sample stage (step S208). Therefore, the pattern for alignment 117 formed on the sample supporting member 115 is disposed in a range within the initial field of view at the time of SEM image capturing. When capturing of an initial field-of-view image is performed in this state (step S209), an observation image of the pattern for alignment 117 can be obtained.

Subsequently, observation image data of the obtained observation image is read to the position magnification calculating unit 127 to calculate positional information with the pattern coordinates using the pattern data (step S210), thereby performing calibration on the stage position of the sample stage 118 and magnification (step S211).

After the calibration, at least one OM image or more captured in the previous OM imaging flow is read to be displayed in a display unit 150 (step S212). The read OM image is processed in the position magnification calculating unit 127 similarly, thereby storing positional information relative to the pattern coordinates.

Finally, the user selects an OM image which the user wants to observe in the same field of view using an operation unit 151 from the OM image displayed (step S213). Then, the field-of-view alignment unit 132 controls an electron optical system 108 and a sample stage 118 (step S214), and imaging in the same field of view as the selected OM image is started (step S215).

As described above, the SEM in the example disposes the pattern for alignment 117 in the initial field of view in electron microscope observation using the sample supporting member 115 capable of being used in common to the case of OM observation, so that it is possible to perform observation in the same field of view as the field of view of the OM image without requiring field-of-view searching and a position magnification calibration work performed manually by the user.

<Sample Supporting Member>

FIGS. 3A and 3B are views illustrating a structure of the sample supporting member 115, wherein FIG. 3A is a schematic bird's eye view and FIG. 3B is a top view.

The sample supporting member 115 is, for example, a flat plate formed of a material such as quartz and metal. In this example, the shape of the plate is a circle, but the shape may be a triangle, a quadrangle, a polygon, or the like. The plate may be a cover glass having a thickness of about 0.04 mm to 0.6 mm which is generally used for OM observation or may be a slide glass having a thickness of about 0.8 mm to 1.5 mm, and the shape of the plate is not particularly limited. When the sample 112 is placed on the flat plate, and the sample 112 is observed with the charged particle beam device, it is necessary that the sample 112 and the sample supporting member 115 have conductivity, but when the sample 112 and the sample supporting member 115 do not have conductivity, a conductive material such as osmium, indium tin oxide (ITO), gold, platinum, carbon, polythiophene, or ionic liquid may be coated on the sample 112 or the sample supporting member 115 to impart conductivity. Regarding the coating to be used, any material may be appropriately selected so as not to influence in charged particle device observation, and the material for conductive coating is not particularly limited.

As illustrated in FIG. 3B, the plate is provided with a pattern for alignment 117 constituted by a grid pattern 133, an address marker 135, and a central marker 134. In addition, a front and back direction recognition marker 136 is also provided so that the user can easily recognize the front and back sides and the direction of the sample supporting member when replacing the sample. Each of the pattern and the marker may be any pattern and marker which are capable of being observed by the OM and the charged particle beam device, and a forming method thereof may be printing, engraving or punching.

The grid pattern 133 is used to calculate magnification of an observation image and a rotation angle of the sample supporting member 115 when performing position calculation. In the present example, a grid pattern is illustrated in which respective grid lines are aligned at a fixed interval and are orthogonal to each other. However, the grid pattern 133 may be any grid pattern with which the feature points such as the grid spacing and the rotation angle can be analyzed, for example, and may be a pattern in which points or symbols are aligned at equal intervals, and the grid pattern is not particularly limited.

The address marker 135 is used to calculate positional information of the sample supporting member when performing position calculation. In this example, although a circle frame is disposed at the intersection of the grid lines and an alphabet recognition symbol is assigned thereto, the frame may be a triangle or a quadrangle, and the recognition symbol may be any symbol such as a numeral, a character, a symbol, or the like, as long as each address can be recognized with the symbol, and its shape is not particularly limited.

The central marker 134 is used to calculate the positional deviation amount between the initial observation field-of-view center and the central marker 134 of an observation image when performing position calculation. When the sample supporting member 115 is placed on the sample holder 116, since the central marker 134 is configured such that the rotational axis of the sample placement portion 137 coincides with the central marker 134 as illustrated in FIG. 4A, the central marker 134 can be observed substantially at the center of the initial field of view even in the case of high magnification imaging, whereby it is possible to start position calculation processing without moving the field of view. In the example, the shape of the central marker 134 is formed in a star shape, but the shape may be circular, semicircular, triangular, quadrangular, or the like, and any shape can be used as long as it enables to recognize the center point in the grid pattern 133. In the case where the shape is a shape exhibiting rotational symmetry, it is more preferable to add a symbol to make the direction recognizable inside or around the center marker 134.

Generally, since the user places the sample supporting member 115 on the sample holder 116 such that the observation field of view and the grid pattern 133 are flush with each other, a rotation angle of the sample supporting member 115 with respect to the observation field of view falls within the range of at most −10 degrees to +10 degrees. If the rotation angle exceeds 90 degrees, the direction of the sample supporting member 115 may be erroneously recognized only by the center marker 134 and the grid pattern 133 having shapes exhibiting rotational symmetry. Therefore, a sample supporting member with a symbol enabling the sample holder 116 illustrated in FIG. 4A, it is possible to calculate the rotation angle of the sample supporting member 115 accurately.

The front and back direction recognition marker 136 is provided such that the user can easily recognize the front and back sides and the direction of the sample supporting member 115. In the example, the shape of marker is set to the alphabet "F", but the shape may be set to "B, G, R, P, or the like" or a similar symbol or figure may be used, and the shapes thereof are not particularly limited as long as the shape facilitates recognition of the front and back sides and the direction.

FIG. 3C is a view illustrating a positional relationship between the sample supporting member 115 and the sample 112 placed on the sample supporting member 115. The sample 112 is placed in the area of the pattern for alignment 117 provided on the sample supporting member 115. In the example, even when the sample 112 is placed on the grid pattern 133 or the central marker 134 in the pattern for alignment 117, it is possible to observe the grid pattern 133 or the central marker 134 under the sample 112.

Generally, when observing a biological sample by OM observation, it is possible to easily observe the pattern under the sample 112 by adjusting the intensity of a light source used for illumination. Incidentally, in electron microscope measurement, the energy of the electrons of the electron beam 106 can be adjusted by changing the acceleration voltage and electrons having sufficiently high energy for the thickness of the sample 112 can pass through the sample 112. Therefore, by setting an acceleration voltage such that the electron beam 106 can pass through the sample 112, the electron beam 106 passes through the sample 112, thereby detecting a signal 113 generated from the pattern positioned under the sample 112. Further, the acceleration voltage is changed to reduce the energy of the electrons so as not to pass through the sample 112, so that it is possible to observe the surface of the sample 112. Accordingly, the sample 112 does not necessarily need to be placed while avoiding the center marker 134, and can be placed at an arbitrary position.

<Sample Holder>

FIGS. 4A and 4B illustrate one configuration example of the sample holder 116, wherein FIG. 4A is a schematic bird's eye view and FIG. 4B is a sectional view taken along line A-A' in FIG. 4A.

The sample holder 116 includes the sample placement portion 137 on which the sample supporting member 115 is placed, a sample base portion 141 serving as the base of the sample placement portion 137, and the sample cover portion 140 fixing the sample supporting member 115.

For improving the efficiency of the sample replacement work, a counterbore part having the same thickness as the sample supporting member 115 to be used during observation is provided on the top surface of the sample placement portion 137 so that the sample supporting member 115 and the sample placement portion 137 are substantially flush with each other. However, the depth of the counterbore part and the thickness of the sample supporting member 115 may not be the same. When mounting the sample cover portion 140, the sample cover portion 140 presses the sample supporting member 115 from the top surface direction, and the sample placement portion 137 is lowered by the extent of the thickness of the sample supporting member 115, and thus the height of the top surface of the sample supporting member 115 may always coincide with the height of the sample base portion 141, which is not particularly limited. By installing the sample supporting member on the counterbore part, alignment between the rotational axis of the sample placement portion and the central marker provided on the sample supporting member is performed. In addition, it is preferable that "coincidence" described here is exact coincidence, but the positional deviation in the range of the depth of focus in the initial field of view is allowed as an error range.

The sample placement portion 137, the sample base portion 141, the sample cover portion 140, and the like constituting the sample holder 116 are made using a material such as SUS316 in this example, but the material is not particularly limited as long as the material is SUS304, Al, C (graphite), Cu, Ta, Mo, Ti, W, brass, bronze, a compound or an alloy containing these substances, and the like, and has electrical conductivity but is a nonmagnetic material.

The sample placement portion 137 includes the rotary knob 139, and is configured such that the sample supporting member 115 placed on the sample placement portion 137 is rotated or held in an arbitrary angle while being flush with the top surface of the sample base portion 141 by operating the rotary knob 139.

The rotational axis of the sample placement portion 137 is configured to coincide with the center of the sample supporting member 115. Further, the sample placement portion 137 is assembled to the sample base portion 141 such that the rotational axis thereof coincides with the optical axis of the electron optical system 108 of the SEM 101 when the sample holder 116 is installed on the mounted part 119 of the sample stage 118. Accordingly, even when the user rotates sample placement portion 137 at any angle in 360 degrees in order to align the horizontal direction of the sample supporting member 115 with the horizontal direction of the sample holder 116, since the center of the sample supporting member 115 always coincides with the optical axis of the electron optical system 108, it is possible to apply a calibration method to be described later. In addition, it is preferable that "coincidence" described here is exact coincidence, but the positional deviation in the range of the depth of focus in the initial field of view is allowed as an error range.

In this example, the outer circumference of the rotary knob 139 is subjected to knurling in order to facilitate the rotation operation, but the form for easily performing a rotation operation such as knurling the outer circumference, forming a groove for using a plus, minus, or hex type driver, or the like is not particularly limited.

The sample cover portion 140 fixes the sample supporting member 115 placed on the sample placement portion 137 by pressing the sample supporting member in a direction from the top surface of the sample base portion 141 to the bottom surface. For fixing, the back surface of the sample cover portion 140 is brought into close contact with the top surface of the sample base portion 141, thereby fixing the sample cover portion 140 with a cover fixing screw 142 provided on the sample base portion 141. In the example, as illustrated in the sectional view of FIG. 4B, springs 143 are arranged around the rotational axis of the sample placement portion 137. The contact surface of the end turn part of each spring 143 with the sample base portion 141 and the sample placement portion 137 is always applied with pressure by the spring 143, and the sample cover portion 140 is fixed to the sample base portion 141, and thus the height of the top surface of the sample supporting member 115 and the height of the top surface of the sample base portion 141 coincide with each other, whereby fixing the sample supporting member 115 with pressure by the spring 143 so as not to move due to vibration or the like.

In addition, the sample cover portion 140 is formed with a window 144 so that the sample 112 and the sample supporting member 115 can be observed therethrough, and the periphery of the window 144 is subjected to embossing in this example in order to secure good electrical conductivity with the top surface of the sample supporting member 115 and to facilitate physical contact. However, the processing is not limited to embossing, the burr of the punched hole may be used, the spring shape may be formed, or the pawl shape may be formed, and the shape for facilitating the contact is not particularly limited. Further, in the example, in order to facilitate checking the rotation direction of the sample supporting member 115, an orientation flat 145 is provided which represents the horizontal direction in initial field of view when performing observation with the SEM 101, but the shape may be a notch shape or the like, the direction of the shape may be a vertical direction, the direction may be of 15 degrees, 30 degrees, 45 degrees, 60 degrees, 75 degrees or the like, and the shape for facilitating checking the rotation direction is not particularly limited.

In order to secure a favorable electric contact between the top surface of the sample supporting member 115 and the sample base portion 141, although SUS316 is used in the present example, the material constituting the sample cover portion 140 and the cover fixing screw 142 is not particularly limited as long as the material is SUS304, Al, Cu, Ta, Mo, Ti, W, brass, bronze, and a compound or an alloy containing these substances, and the like, has electrical conductivity, and can avoid scuffing of the screw by applying lubricant such as $MoS_2$, $WS_2$, and the like and mixtures containing these substances on the cover fixing screw 142.

The sample base portion 141 includes a fitted part (not illustrated) for mounting the sample holder 116 on the mounted part 119 of the sample stage 118 and a cover fixing screw 142.

Although the top surface of the sample base portion 141 is subjected to V-shaped groove processing 138 in the horizontal direction and the vertical direction in the present example in order to align the horizontal direction of the pattern for alignment 117 formed on the sample supporting member 115 and the horizontal direction in the initial imaging field of view when performing observation with the SEM 101, the groove processing 138 may be performed in only the horizontal direction or in only the vertical direction, in a direction of 15 degrees, 30 degrees, 45 degrees, 60 degrees, 75 degrees, or the like, the direction may be one direction with respect to the rotational axis of the sample placement portion 137, or the sectional shape may have a U shape, a W shape, a laterally-inverted C shape, or a concave part similar to those, and the shape for facilitating checking the rotation direction is not particularly limited.

FIG. 4C illustrates a schematic bird's eye view of the sample holder including three sample placement portions. The sample placement portion 137 may be provided in plural with respect to the sample holder 116 as long as at least one sample placement portion or more is provided, but the number of sample placement portions is not particularly limited. The sample holder 116 includes the sample placement portion 137, the groove processing 138 (not illustrated), the rotary knob 139, the sample cover portion 140, the sample base portion 141, the cover fixing screw 142 (not illustrated), the spring 143 (not illustrated), the window 144 (not illustrated), and the orientation flat 145 (not illustrated).

When performing an electron microscope observation work using the sample holder 116 including a plurality of sample placement portions, by the movement in the XY plane of the sample stage 118 (in the plane formed by the x direction perpendicular to the electron beam 106 and the y direction orthogonal to the electron beam 106 and perpendicular to the x direction), a sample moving device controller controls the movement of the stage such that the center of the sample placement portion 137 selected through the operation unit 151 by the user falls within the initial field of view of the SEM image. The center position of each sample placement portion 137 is recorded in the control device 105, and the stage is controlled such that the center position of the sample placement portion 137 arbitrarily selected by the user becomes the initial field-of-view center. With this movement control, even when the sample holder 116 including the plurality of sample placement portions 137 is used, it is possible to always check the pattern for alignment 117 on the sample supporting member 115 in the initial field of view, whereby it is possible to perform position magnification calculation.

<Position Magnification Calculating Unit>

FIG. 5A is a view illustrating a positional relationship between the initial field of view (field of view of SEM 146) of the SEM image and the SEM image field-of-view center 147m and the pattern for alignment 117 (133, 134, and 135), and FIG. 5B is a view for describing a positional relationship between pattern data 148 constituted of the shape data and the coordinate data of the pattern for alignment 117 and the field of view of SEM 146.

The position magnification calculating unit 127 reads image data of the SEM image and the OM image and calculates the observation magnification in each of the observation image and the relative positional information of the pattern coordinates and the field-of-view position by using the pattern data 148 which is stored in the pattern data storage unit 126 and is constituted of the shape data and the coordinate data of the pattern for alignment 117. For calculating the observation magnification, the grid pattern 133 is used, and for calculating the positional information, the central marker 134 is used in the case of the SEM image, and the central marker 134 or the address marker 135 is used in the case of the OM image.

Hereinafter, an operation example in the case of reading an SEM image will be described with reference to FIGS. 5A and 5B and FIG. 6 as one operation example of the position magnification calculating unit 127 of the example.

FIG. 6 is a flow chart illustrating an operation of the position magnification calculating unit.

When the operation is started (step S301), first, shape data of the pattern for alignment 117 is read from the pattern data storage unit 126 (step S302). The shape data includes grid spacing of the grid pattern 133, shape data of the central marker 134, shape data of the address marker 135, and position coordinate data of the grid pattern 133 or each marker.

Next, reading of SEM image data which is an observation image with the initial field of view of SEM and captured in step S209 is performed (step S303). As illustrated in FIG. 5A, in the SEM image, the central marker 134 and the grid pattern 133 are necessarily observed within the field of view of SEM 146.

Subsequently, the SEM image data is analyzed to calculate spacing and a rotation angle of the grid pattern (step S304). Specifically, for example, a straight line of the grid pattern 133 is recognized from the SEM image data by using well-known image processing such as Hough transformation, pattern matching and the like, and an image recognition technique to calculate the inclination of the straight line, thereby calculating the rotation angle. In addition, the grid spacing is calculated by, for example, measuring the distance between at least two parallel straight lines.

Subsequently, the grid spacing obtained in step S304 and the actual known spacing of the grid pattern 133 are compared to each other, thereby calculating an observation magnification of the SEM image data (step S305).

After the observation magnification is calculated, the positional deviation amount between the central marker 134 and the SEM image field-of-view center 147 is calculated (step S306). Specifically, the central marker 134 is recognized by, for example, using a well-known image recognition technique such as pattern matching to calculate the positional deviation amount.

Since the rotation angle, the observation magnification, and the positional deviation amount of the SEM image field of view have already been obtained through the steps S304, S305, and S306 so far, the relative position of the pattern for alignment 117 and the SEM image field of view in the subsequent step (step S307).

As illustrated in FIGS. 5A and 5B, the coordinate system of the field of view of SEM is set to a field-of-view coordinate system (X, Y coordinate system), and the coordinate system of the pattern data 148 is set to a pattern coordinate system (X', Y' coordinate system), so that the SEM field-of-view position is set to E(X, Y). In this state, when the rotation angle of the SEM image field of view is set to θ, the observation magnification is set to M, and the positional deviation amount is set to S, a position coordinate E(X', Y') of the field of view of SEM in the pattern coordinate system can be expressed using a conversion function T(θ, M, S) as follows.

$$E(X',Y')=E(X,Y)T(\theta,M,S)$$

Thereby, it is possible to calculate the relative position of the pattern for alignment 117 and the SEM image field of view.

Finally, position calibration of the sample stage 118 and magnification calibration of the electron optical system 108 are performed (step S308) to transmit relative position data to the field-of-view alignment unit (step S309).

Hitherto, one operation example in the case of reading the SEM image has been described. When the OM image is read, an image recognition target in step S306 is subjected to image recognition processing as at least one of the central marker 134 or the address marker 135, and step S308 is omitted.

As described above, the position magnification calculating unit 127 operates to calculate relative positional information, and thus the SEM system in the example can realize alignment between an OM image and a field of view by only imaging once with the initial field of view.

Hitherto, according to the example, it is possible to provide a charged particle beam device including a charged particle source, a sample holder placed with a sample thereon, a charged particle beam optical system in which the sample is irradiated with a charged particle emitted from the charged particle source as a charged particle beam, a detector detecting a signal emitted from the sample, and a controller controlling each constituent element, wherein the sample holder includes a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle, a sample base portion including an opening through which the sample placement portion is capable of moving vertically and a second top surface around the opening, and a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other.

In addition, it is possible to provide a charged particle beam device including a charged particle source, a sample holder placed with a sample, a charged particle beam optical system in which the sample is irradiated with a charged particle emitted from the charged particle source as a charged particle beam, a detector detecting a signal emitted from the sample, and a controller controlling each constituent element, wherein the sample holder includes a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle, a sample base portion including an opening through which the sample placement portion is capable of moving vertically and a second top surface around the opening, and a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other, the controller includes a first image processor which processes first imaging data including a pattern for analyzing the magnification and rotation angle of the sample supporting member obtained by using an optical microscope and the central marker or the address marker, a second image processor which processes second imaging data including a pattern for analyzing the magnification and rotation angle of the sample supporting member obtained by using a detector and the central marker, a pattern data storage unit in which pattern data including shape data and coordinate data of the pattern for alignment is stored, and a position magnification calculating unit which calculates observation magnification using the first image data processed by the first image processor, the second image data processed by the second image processor, and the pattern data stored in the pattern storage unit, and relative positional information of pattern coordinates and a field-of-view position.

In addition, it is possible to provide the sample holder including a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle, a sample base portion including an opening through which the sample placement portion is capable of moving vertically and a second top surface around the opening, and a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other.

As described above, according to the example, it is possible to provide a charged particle beam device and a sample holder capable of easily searching for an observation field of view. In particular, in a charged particle beam device performing field-of-view searching using an observation position designation image captured with the OM and a sample holder used therefor, imaging of a reference image for calibration or feature point associating work is eliminated, thereby reducing the number of operations of the user or easily observing the same field of view as the field of view of images captured with OM. Further, specification of magnification when the imaging device captures a captured image of the sample, or recognition of the position of the sample supporting member in the captured image can be performed fast and easily, or with higher accuracy, whereby it is possible to reduce a time that the user spends to search for a field of view.

It should be noted that the present invention is not limited to the above-described examples, but includes various modified examples. For example, the above-described examples have been described in detail in order for better understanding the present invention, and the examples are not necessarily limited to those having all the configurations described above. Further, it is possible to add or replace other configurations for a part of a certain configuration.

REFERENCE SIGNS LIST

101: SEM, 102: Electron beam column, 103: Sample chamber, 104: Microscope body, 105: Control device (controller), 106: Electron beam, 107: Electron gun, 108: Electron optical system, 109: Condenser lens, 110: Deflector, 111: Objective lens, 112: Sample, 113: Signal, 114: Detector, 115: sample supporting member, 116: Sample holder, 117: Pattern for alignment, 118: Sample stage, 119: Mounted part, 120: Sample moving mechanism, 121: OM, 122: Stage, 123: Imaging element, 124: Image processor for OM (first image processor), 125: Image processor for SEM (second image processor), 126: Pattern data storage unit, 127: Position magnification calculating unit, 128: Magnification calculating unit, 129: Position calculating unit, 130: Electron optical system controller, 131: Sample stage controller, 132: Field-of-view alignment unit, 133: Grid pattern, 134: Central marker, 135: Address marker, 136: Front and back direction recognition marker, 137: Sample placement portion, 138: Groove processing, 139: Rotary knob, 140: Sample cover portion, 141: Sample base portion, 142: Cover fixing screw, 143: Spring, 144: Window, 145: Orientation flat, 146: Field of view of SEM, 147: SEM image field-of-view center, 148: Pattern data, 150: Display unit, 151: Operation unit

The invention claimed is:

1. A charged particle beam device comprising a charged particle source, a sample holder placed with a sample thereon, a charged particle beam optical system in which the sample is irradiated with a charged particle emitted from the charged particle source as a charged particle beam, a detector detecting a signal emitted from the sample, and a controller controlling each constituent element, wherein
the sample holder includes
a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle,
a sample base portion including an opening through which the sample placement portion is capable of moving vertically and a second top surface around the opening, and
a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other.

2. The charged particle beam device according to claim 1, wherein
the pattern for analyzing the magnification and rotation angle is a grid pattern.

3. The charged particle beam device according to claim 1, wherein
the sample supporting member further includes a front and back direction recognition marker.

4. The charged particle beam device according to claim 1, wherein
the sample supporting member is made of an insulative material and is formed with a conductive coating on a surface thereof.

5. The charged particle beam device according to claim 1, wherein
the charged particle beam device further includes a sample moving mechanism which displaces a position or an orientation of the sample holder or both thereof.

6. The charged particle beam device according to claim 1, wherein
the sample holder includes a plurality of sets of the sample placement portion and the sample cover portion.

7. A charged particle beam device comprising a charged particle source, a sample holder placed with a sample, a charged particle beam optical system in which the sample is irradiated with a charged particle emitted from the charged particle source as a charged particle beam, a detector detecting a signal emitted from the sample, and a controller controlling each constituent element, wherein
the sample holder includes
a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle,
a sample base portion including an opening through which the sample placement portion is capable of moving vertically and a second top surface around the opening, and
a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other,
the controller includes
a first image processor which processes first imaging data including a pattern obtained by using an optical microscope for analyzing the magnification and rotation angle of the sample supporting member and the central marker or the address marker,
a second image processor which processes second imaging data including a pattern obtained by using a detector for analyzing the magnification and rotation angle of the sample supporting member and the central marker,
a pattern data storage unit in which pattern data including shape data and coordinate data of the pattern for alignment is stored, and
a position magnification calculating unit which calculates observation magnification using the first image data processed by the first image processor, the second image data processed by the second image processor, and the pattern data stored in the pattern data storage unit, and relative positional information of pattern coordinates and a field-of-view position.

8. The charged particle beam device according to claim 7, wherein
the controller further includes a field-of-view alignment unit which calculates positional information for obtaining the same field of view as the field of view obtained with the optical microscope.

9. The charged particle beam device according to claim 7, wherein
the sample holder includes a plurality of sets of the sample placement portion and the sample cover portion, and
the controller is recorded with center position of each sample placement portion.

10. A sample holder comprising:
a sample placement portion including a first top surface on which a counterbore part is formed and a rotational axis for rotating the first top surface horizontally, the counterbore part being aligned by being mounted with a sample supporting member having a pattern for alignment including a central marker and a pattern and an address marker for analyzing magnification and a rotation angle;

a sample base portion including an opening through which the sample placement portion is capable of moving vertically and a second top surface around the opening; and a sample cover portion which has conductivity, includes a window through which the pattern for alignment of the sample supporting member is exposed, and is pressed down toward a direction of the second top surface of the sample base portion, so that a top surface of the sample supporting member placed on the sample placement portion and the second top surface are flush with each other.

11. The sample holder according to claim 10, wherein the counterbore part of the sample placement portion is a portion for performing alignment between the central marker of the sample supporting member and the rotational axis of the sample placement portion.

12. The sample holder according to claim 10, wherein the sample holder includes a plurality of sets of the sample placement portion and the sample cover portion.

* * * * *